United States Patent [19]

Kamachi et al.

[11] 4,429,996
[45] Feb. 7, 1984

[54] PROCESS OF FRACTIONATING ELECTROPHORETOGRAM SIGNALS

[75] Inventors: Shinichi Kamachi, Hino; Toshihide Fujiwara, Fuchu, both of Japan

[73] Assignee: Olympus Optical Co. Ltd., Tokyo, Japan

[21] Appl. No.: 256,591

[22] Filed: Apr. 22, 1981

[30] Foreign Application Priority Data

Apr. 23, 1980 [JP] Japan .................................. 55-52808

[51] Int. Cl.³ .......................................... G01N 27/28
[52] U.S. Cl. .................................................. 356/344
[58] Field of Search ........................................ 356/344

[56] References Cited

PUBLICATIONS

Fisher et al., "Calculus and Analytic Geometry", pp. 131–135, Prentice-Hall, published prior to 1963.

Primary Examiner—Bruce Y. Arnold
Attorney, Agent, or Firm—Parkhurst & Oliff

[57] ABSTRACT

To facilitate fractionation of an electrophoretogram, the disclosed process differentiates signals representing the electrophoretogram so as to obtain the differential of the first order and to generate a first series of pulses representing changes of sign of the differential of the first order. The process differentiates again the differential of the first order so as to obtain the differential of the second order and generates a second series of pulses representing changes of sign of the differential of the second order. Output pulses are generated by logically processing the first and second series of pulses, whereby the electrophoretogram is fractionated on the basis of the timing of the output pulses.

2 Claims, 8 Drawing Figures

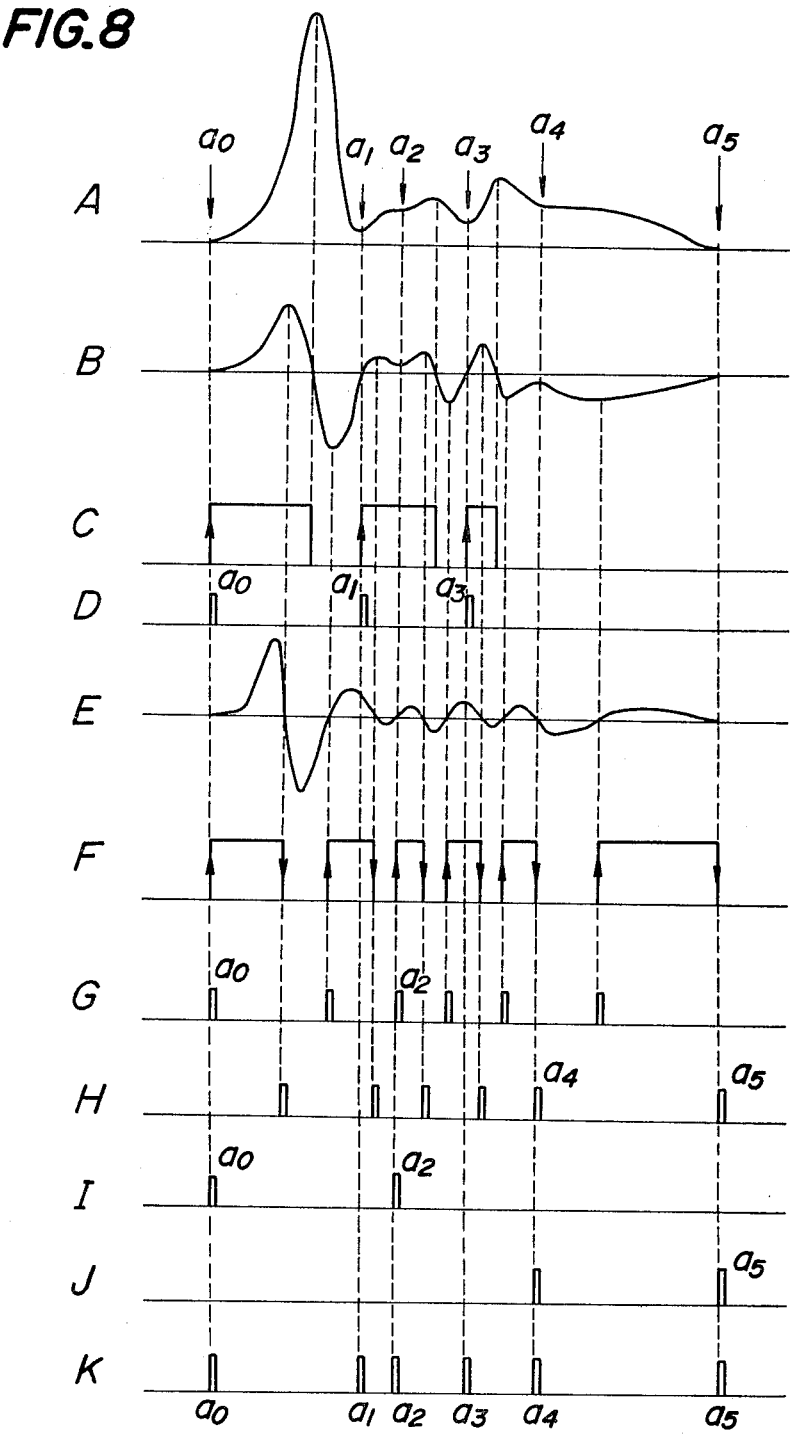

PROCESS OF FRACTIONATING ELECTROPHORETOGRAM SIGNALS

BACKGROUND OF THE INVENTION

1. Field of the Invention

This invention relates to a process of fractionating electrophoretogram signals.

2. Description of the Prior Art

Electrophoresis has been used for isolation and analysis of substances. As an example, isolation of various components in serum proteins by electrophoresis will be explained. Usually, a concentration pattern of serum protein which is obtained by electrophoresis has a plurality of maxima and minima. The concentration pattern is generally fractionated into five fractions; namely, albumin (Alb) fraction, $\alpha_1$-globulin fraction, $\alpha_2$-globulin fraction, $\beta$-globulin fraction and $\gamma$-globulin fraction. The boundary positions of different components are determined by detecting the minima in the density pattern. More particularly, the boundary points are determined by an electric process based on the fact that the differential of the concentration versus time pattern is zero at the minima. Such an electric process of the prior art has a shortcoming. As long as the concentration pattern has clearly defined minima the process functions satisfactorily. If the boundary positions of adjacent fractions are not minima, but merely points of inflection due to the nearness of adjacent maxima of the concentration pattern or other reasons, the differential of the concentration pattern is not zero at such non-minimum points of inflection so that the boundary positions between adjacent fractions cannot be determined.

SUMMARY OF THE INVENTION

Therefore, an object of the present invention is to obviate the aforesaid shortcoming of the prior art, by providing an impoved process for fractionating electrophoretogram signals in which the process detects either minima or points of inflection.

To accomplish the aforesaid object according to the present invention, electrophoretogram signals from an electrophoretic detector are differentiated to derive differential signals of the first order and to obtain a first series of logic signals depending on the sign or polarity of said differential signals of the first order Differential signals of the first order are differentiated again so as to derive differential signals of the second order and to obtain a second series of logic signals depending on the sign or polarity of the differential signals of the second order. The output logic signals are derived by logically treating said first and second series of logic signals, said output logic signals being used to determine boundary positions to fractionate said electrophoretogram signals.

BRIEF DESCRIPTION OF THE DRAWINGS

For a better understanding of the invention, reference is made to the accompanying drawings, in which:

FIG. 8 shows waveforms of signals at various points in the apparatus of FIG. 7.

Throughout different views of the drawings, 1 is an electrophoretic detector, 2, 6 are differentiating circuits, 3, 7 are comparator circuits, 4, 8 are pulse shaping circuits, 5 is an output terminal, 9, 9' are AND circuits, 10 is an OR circuits, and 11 is a NOT circuit.

DESCRIPTION OF THE PREFERRED EMBODIMENT

Figure 1:
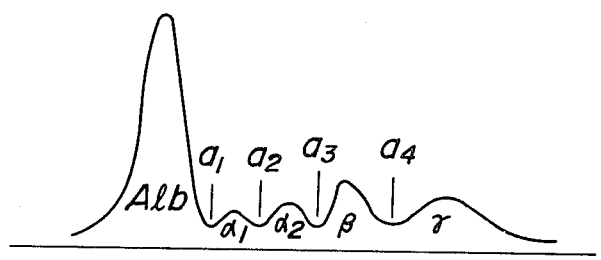
FIGS. 1 and 2 are curved representing electrophoretogram signals to be used in the description of the fractionating operation of a process according to the present invention.
Figure 3:
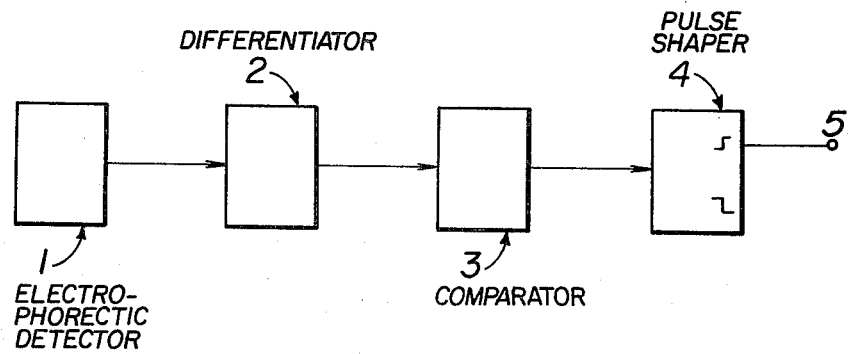
FIG. 3 is a block diagram of an apparatus for carrying out a fractionating process of the prior art.
Figure 4:
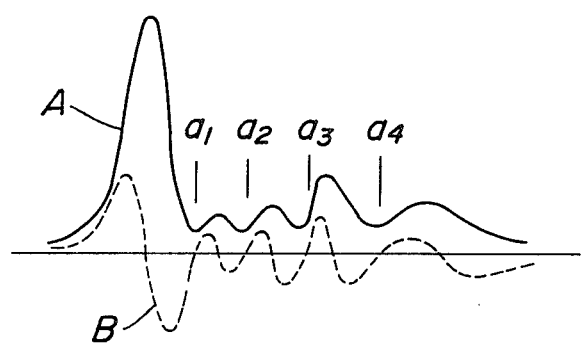
FIGS. 4 and 5 are curves showing electrophoretogram signals and signals representing differentials of first order thereof, which curves are used in the description of the invention.

Before entering the details of the invention, the prior art will be briefly reviewed. Referring to FIG. 1 showing a curve representing a concentration pattern of serum proteins as an example of electrophoretogram signals, boundary positions among five fractions thereof, namely albumin (Alb) fraction and $\alpha_1$-, $\alpha_2$-, $\beta$-, and $\gamma$-globulin fractions, are clearly defined by minima $a_1$, $a_2$, $a_3$, and $a_4$. Thus, the aforesaid boundary positions can be determined through an electric process which derives differentials of first order of the concentration pattern curve, so as to detect zero-value points of the thus derived differentials. FIG. 3 shows an apparatus of the prior art for detecting the minima. In this apparatus, an electrophoretic detector 1 produces electrophoretogram signals, such as the solid line curve a of FIG. 4, and a differentiating circuit 2 differentiates the signals of the curve a so as to derive signals of differentials of first order as shown by the dotted line curve B of FIG. 4. Such signals of differentials are compared with a zero level reference value at a comparator circuit 3 and converted into pulse signals corresponding to positive portions of the signals of the differentials. The pulse signals from the comparator circuit 3 are applied to a pulse shaping circuit 4 which produces output pulse signals at an output terminal 5. The output pulse signals represent the timing when the aforesaid signals of the differentials vary from a negative value to a positive value. Thus, the boundary positions $a_1$, $a_2$, $a_3$, and $a_4$ are determined by the timing of the output pulse signals at the output terminal 5.

Figure 2:
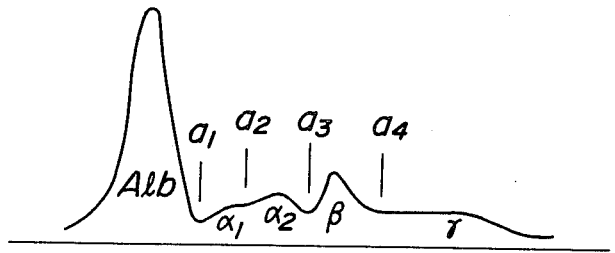
Figure 5:
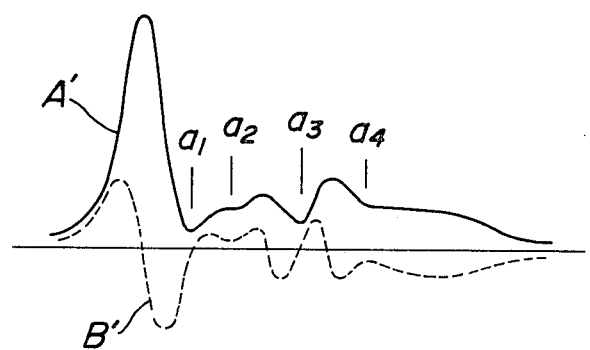

It is noted that such process of the prior art is effective only when the electrophoretogram or concentration pattern has clearly defined boundary position among various components in the form of distinct maxima or minima, for instance, as shown by the minima of FIG. 1. However, the boundary positions of different components are sometimes not so clear due to various reasons, for instance overlapping of a curve portion for one component with that for another component depending on the kinds and amounts of different proteins in serum. In another example shown in FIG. 2, the boundary $a_2$ between $\alpha_1$- and $\alpha_2$-globulin fractions and the boundary $a_4$ between $\beta$- and $\gamma$-globulin fractions are not clear. In the case of a concentration pattern shown by the solid line curve A' of FIG. 5, differentials of first order of the concentration pattern curve do not assume zero at similar boundary positions $a_2$ and $a_4$ as shown by the dotted line curve B'. Accordingly, the process of the prior art cannot determine non-minimum boundary positions such as the aforesaid boundary positions $a_2$ and $a_4$.

Figure 6:
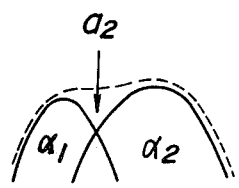
FIG. 6 is a fractional diagram of a concentration pattern being used in the description of the invention.

Referring to FIG. 6, if concentration peaks for the $\alpha_1$-globulin fraction and $\alpha_2$-globulin fraction are near to each other, there is no distinct valley or minimum between the $\alpha_1$- and $\alpha_2$-globulin fractions as shown by the dash-line of the figure. Nevertheless, the boundary position between the two fractions exists between the two solid line peaks, and the position of such boundary is at the point of inflection of the dash-line curve. Accordingly, when the concentration pattern curve does not have distinct valleys or minima for certain boundary positions, such non-minimum boundary positions can be determined by detecting points of inflection.

The inventors noted the fact that even when distinct minima do not exist between adjacent fractions, the boundary positions between such adjacent fractions can be accurately determined by detecting points of inflection. Whereby, the inventors have succeeded in obviating the aforesaid shortcoming of the prior art.

Figure 7:
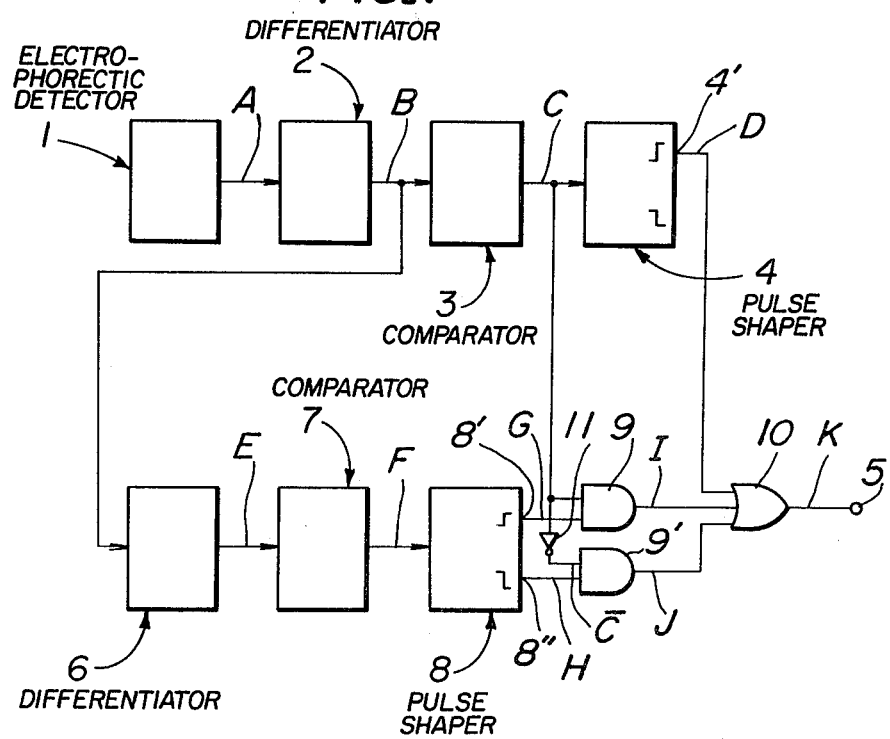
FIG. 7 is a block diagram of an example of apparatus for carrying out the process according to the present invention.

A preferred embodiment of the invention will be now described by referring to FIGS. 7 and 8. An electrophoretic detector 1 produces signals of an electrophoretogram as shown by a pattern curve A of FIG. 8. In the waveform of A, boundary positions $a_0$, $a_1$, and $a_3$ are given by distinct minima, while the boundary positions $a_2$ and $a_4$ are not in the form of clear minima. The signals for the waveform of A are applied to a first differentiating circuit 2 where signals of differentials of the first order are derived as shown by the waveform of B, FIG. 8 the differential signals B of the first order are applied to a first comparator circuit 3. The first comparator circuit 3 is such that pulse signals therefrom assume a constant positive voltage as long as the differential signals B of the first order are positive, namely from a moment when said differential signals B of the first order vary from negative to positive unit a moment when they vary from positive to negative, as shown by pulse signals C of FIG. 8. The pulse signals C are applied to a first pulse shaping circuit 4, and a first set of pulse signals as shown by pulse signals D of FIG. 8 are produced at one output terminal 4' in response to the rising ends of the pulse signals C. In the illustrated example, the first set of pulse signals D are produced at boundary positions $a_0$, $a_1$ and $a_3$, but not at boundary positions $a_2$ and $a_4$.

In the process of the present invention, to detect the boundary positions $a_2$ and $a_4$, zero points of differentials of the second order of the concentration pattern curve A are discriminated both for positive values of the differential signals B of the first order and for negative values of the differential signals B of the first order thereof. To this end, the differential signals B of the first order from the first differentiating circuit 2 are applied to a second differentiating circuit 6. The signals of differentials of the second order of are generated as shown by the waveform E of FIG. 8. The differential signals E of the second order of FIG. 8 are applied to a second comparator circuit 7, so as to produce pulse signals corresponding to positive values of the differential signals E of the second order as shown by pulse signals F of FIG. 8. This is similar to the production of the aforesaid pulse signals C from the first comparator circuit 3. The pulse signals F are applied to a second pulse shaping circuit 8, and a second set of pulse signals are produced at one output terminal 8', as shown by pulse signals G of FIG. 8. The pulse signals G correspond to the rising ends of the pulse signals F representing the variations of the differential signals E of the second order from a negative value to a positive value through zero points. The second pulse shaping circuit 8 also produces a third set of pulse signals at the other output terminal 8'', as shown by pulse signals H of FIG. 8. The pulse signals H correspond to the falling ends of the pulse signals F representing the variation of the differential signals E of the second order from a positive value to a negative value through zero points.

The second and third sets of pulse signals, as shown by the pulse signals G and H of FIG. 8, include not only pulse signals corresponding to the aforesaid boundary positions $a_2$, $a_4$ and if desired $a_5$, but also superfluous pulse signals. Thus, to get the final output pulse signals such superfluous pulse signals must be removed while those signals representing the aforesaid boundary positions $a_0$, $a_1$, $a_3$, and $a_5$ must all be included in the final output pulse signals. To this end, the process of the present invention combines the pulse signals C from the first comparator circuit 3, the first set of pulse signals D from the first pulse shaping circuit 4, and the second and third sets of pulse signals from the second pulse shaping circuit 8, so as to derive the final output pulse signals.

More specifically, the pulse signals C from the first comparator circuit 3 and the second set of pulse signals G produced by the second pulse shaping circuit 8 at one output terminal 8' are applied to a first AND circuit 9. The logical product of the pulse signals C and G provides pulse signals corresponding to the boundary positions $a_0$ and $a_2$ as shown by the pulse signals I of FIG. 8. The inverted pulse signals C produced by inverting the aforesaid pulse signals C by a NOT circuit 11, and the third set of pulse signals H produced by the second pulse shaping circuit 8 at the other output terminal 8'' are applied to a second AND circuit 9'. The logical product of the pulse signals C and H provides pulse signals corresponding to the boundary position $a_4$ and $a_5$, as shown by the pulse signal J of FIG. 8. The pulse signals I and J thus obtained are applied to an OR circuit 10, to which the first set of pulse signals D obtained by the first pulse shaping circuit 4, are also applied. The output signals produced at the output terminal 5 of the OR circuit 10 now include those pulses which correspond to the boundary positions $a_0$ through $a_5$, as shown by the pulse signals K of FIG. 8.

When the timing or positions of the individual pulses of the output pulse signals K thus obtained are measured, boundary positions between adjacent fractions of electrophoretogram signals are accurately identified and determined regardless of whether the boundary positions are in the form of distinct valleys or indistinct points of inflection.

In the foregoing description, the two points $a_0$ and $a_5$ in the concentration pattern curve A of FIG. 8 are treated as boundary positions, but it is also possible to treat the two points as the starting and terminating points of the concentration pattern or electrophoretogram and not as the boundary positions thereof.

The formations of individual elements in the apparatus of FIG. 7 are obvious to those skilled in the art, so that detailed formations of such individual elements will not be described here.

It should be noted here that the process of fractionating electrophoretogram signals according to the present invention can be carried out by developing it into computer software without using any apparatus such as that shown in FIG. 7. In the case of using the process of the invention in the computer software, the eectrophoretogram signals must be converted into digital signals by an analog-digital converter means, so that the thus converted digital signals are delivered to a computer for storage therein. The digital signals thus stored in the computer can be numerically processed through similar steps to those described hereinbefore by referring to the apparatus of FIG. 7, whereby the boundary positions for fractionating the electrophoretogram signals can be determined by computer calculations.

Although the invention has been described with a certain degree of particularity, it is understood that the present disclosure has been made only by way of example and that numerous changes in details of combination and arrangement of steps may be resorted to without departing from the scope of the invention as hereinafter claimed.

What is claimed is:

1. A process of fractionating electrophoretogram signals, comprising the steps of: differentiating the electrophotogram signals from an electrophoretic detector so as to obtain differential signals of the first order; deriving a first series of logic signals depending on the sign of said differential signals of the first order; differentiating said differential signals of the first order so as to obtain differential signals of the second order; deriving a second series of logic signals depending on the sign of said differential signals of said order; and producing output logic signals which determine positions to fractionate said electrophoretogram signals, by deriving logical additions of (i) pulses representing rising ends of said first series of logic signals, (ii) the logical product of said first series of pulse signals and pulses representing rising ends of said second series of logic signals, and (iii) the logical product of signals obtained by inverting said first series of pulse signals and pulses representing the falling ends of said second series of pulse signals.

2. A process according to claim 1, wherein said step of deriving the first series of logic signals comprises comparing the differential signals of the first order with a zero-volt reference voltage and generating the first series of logic signals when the differential signals of the first order are equal to or higher than said zero volt reference signal, and said step of deriving the second series of signals comprises comparing the differential signals of the second order with said zero-volt reference voltage and generating the second series of signals when the differential signals of the second order are equal to or higher than said zero-volt reference voltage.

* * * * *